(12) United States Patent
Callister et al.

(10) Patent No.: US 6,432,116 B1
(45) Date of Patent: *Aug. 13, 2002

(54) OCCLUDING DEVICE AND METHOD OF USE

(75) Inventors: Jeffrey P. Callister, Menlo Park; William S. Tremulis, Redwood City, both of CA (US)

(73) Assignee: Ovion, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/468,749

(22) Filed: Dec. 21, 1999

Related U.S. Application Data

(63) Continuation of application No. 09/112,085, filed on Jul. 8, 1998, now Pat. No. 6,096,052.

(51) Int. Cl.⁷ .............................. A61F 6/20; A61F 6/22
(52) U.S. Cl. ...................................... 606/157; 606/108
(58) Field of Search ................................ 606/157, 158, 606/108

(56) References Cited

U.S. PATENT DOCUMENTS

| | | | |
|---|---|---|---|
| 3,687,129 A | 8/1972 | Nuwayser | 128/1 R |
| 3,815,578 A | 6/1974 | Bucalo | 128/1 R |
| 3,855,996 A | 12/1974 | Bolduc | 128/1 |
| 4,503,569 A | 3/1985 | Dotter | 3/1.4 |
| 4,606,336 A | 8/1986 | Zeluff | 128/130 |
| 4,733,665 A | 3/1988 | Palmaz | 128/343 |
| 5,163,958 A | 11/1992 | Pinchuk | 623/11 |
| 5,190,546 A | 3/1993 | Jervis | 606/78 |
| 5,197,978 A | 3/1993 | Hess | 623/1 |
| 5,303,719 A | 4/1994 | Wilk et al. | 128/898 |
| 5,366,472 A | 11/1994 | Hillstead | 606/194 |
| 5,382,261 A | 1/1995 | Palmaz | 606/158 |
| 5,423,849 A | 6/1995 | Engelson et al. | 606/191 |
| 5,443,500 A | 8/1995 | Sigwart | 623/1 |
| 5,474,089 A | 12/1995 | Waynant | 128/843 |
| 5,545,210 A | 8/1996 | Hess et al. | 623/1 |
| 5,601,593 A | 2/1997 | Freitag | 606/198 |
| 5,601,600 A | 2/1997 | Ton | 606/206 |
| 5,656,036 A | 8/1997 | Palmaz | 623/12 |
| 5,766,203 A | 6/1998 | Imran et al. | 606/198 |
| 6,176,240 B1 | 1/2001 | Nikolchev et al. | 128/830 |

FOREIGN PATENT DOCUMENTS

| | | |
|---|---|---|
| EP | 0 105 669 | 4/1984 |
| WO | WO 93/06884 | 4/1993 |
| WO | WO 94/24944 | 11/1994 |
| WO | WO 96/40024 | 12/1996 |
| WO | WO 98/26737 | 6/1998 |
| WO | WO 99/15116 | 4/1999 |

*Primary Examiner*—Paul J. Hirsch
(74) *Attorney, Agent, or Firm*—Heller Ehrman White & McAuliffe

(57) ABSTRACT

A device for occluding a body lumen, and particularly contraceptive or sterilization device for occluding a reproductive tract or lumen to prevent the passage of reproductive cells through the tract or lumen, generally comprising a tubular member, and a mesh member, transversely disposed on the tubular member lumen. The mesh member is permeable to allow for tissue ingrowth, which produces a tissue impregnated mesh occluding the body lumen. The occluding device of the invention can be used in the fallopian tubes of a female patient, the vas deferens of a male patient, or other body lumen.

45 Claims, 9 Drawing Sheets

OCCLUDING DEVICE AND METHOD OF USE

This application is a continuation-in-part of application Ser. No. 08/770,123, filed on Dec. 18, 1996 and a continuation of application Ser. No. 09/112,085, filed Jul. 8, 1998, now U.S. Pat. No. 6,096,052, both of which are incorporated herein by reference.

FIELD OF INVENTION

This invention relates to the field of occluding devices and the methods of using such devices, and more particularly to contraceptive and sterilization devices.

BACKGROUND OF THE INVENTION

Conventional contraceptive strategies generally fall within three categories: physical barriers, drugs and surgery. While each have certain advantages, they also suffer from various drawbacks. Barriers such as condoms and diaphragms are subject to failure due to breakage and displacement. Drug strategies, such as the pill and Norplant™, which rely on artificially controlling hormone levels, suffer from known and unknown side-effects from prolonged use. Finally, surgical procedures, such as tubal ligation and vasectomy, involve the costs and attendant risks of surgery, and are frequently not reversible. Thus, there remains a need for a safe, effective method of contraception, particularly a non-surgical method which is reversible.

SUMMARY OF THE INVENTION

This invention is directed to a device for occluding a body lumen, generally comprising a tubular member, and a mesh member transversely disposed on the tubular member which is permeable to allow for tissue ingrowth. The tissue ingrowth produces a tissue impregnated mesh which occludes the body lumen. A presently preferred embodiment is a contraceptive or sterilization device for occluding a reproductive tract or lumen to prevent the passage of reproductive cells through the tract or lumen. For example, the occluding device of the invention can be used in the fallopian tubes of a female patient, or the vas deferens of a male patient. However, the occluding device of the invention can be used in other body lumens or passageways. For example, the occluding device of the invention can be used to repair a cardiac malformation, known as a ventricular septal defect, in which a passageway is formed in the heart wall that separates the right and left ventricles of the heart allowing blood leakage between the two ventricles. Thus, the occluding device of the invention is secured to the heart wall defining the septal defect, and ingrowth of the myocardium into the device mesh member occludes the passageway to thereby repair the defect. Similarly, atrial septal defects or other passageways in the heart and elsewhere in the body may be occluded using the device of the invention.

In accordance with the invention, the tubular member has a first end, a second end, and a lumen extending therein. The mesh member extends transversely on the tubular member, so that cellular invasion through the mesh member occludes the tubular member lumen and, consequently, the body lumen in which it is installed. In a presently preferred embodiment, the mesh member is disposed within the lumen of the tubular member. However, the transversely disposed mesh member may be outside of the tubular member lumen, as for example, where the mesh member comprises an end cap having a peripheral edge connected to an end of the tubular member. The tissue impregnated mesh forms an occluding member with improved durability over synthetic occluders, which are more vulnerable to rupture or failure within the body due to their synthetic structures. Moreover, the occluding device is highly flexible which facilitates the introduction and retention of the device within the body lumen.

In a presently preferred embodiment, the mesh member comprises strands of a material woven or bundled into a permeable structure. However, other suitable permeable structures may be used, including a porous membranal structure which allows for tissue ingrowth. The mesh member is formed from a biocompatible material, such as a metal, polymeric material, and organics such as animal tissues, and is preferably reactive to tissue so as to promote the tissue ingrowth into the mesh member.

Preferably, the tubular member is at least in part expandable within the body lumen from a first configuration suitable for introduction into the body lumen to a second larger configuration to facilitate securing the expanded tubular member to at least a portion of a wall which defines the body lumen. In one presently preferred embodiment, the tubular member has an open or lattice-like framework which allows for the growth of tissue through the openings of the lattice-like framework, so as to interconnect the tubular member and the wall of the body lumen. The surface of the tubular member may be treated to promote the tissue ingrowth.

The occluding device of the invention may be advanced to the desired location within the body lumen by a suitable delivery system, such as a delivery catheter or a conventional balloon catheter similar to those used for delivering stents, aortic grafts and various types of prosthesis. The device is introduced and positioned within the region of the body lumen to be occluded with the tubular member in the first configuration with small transverse dimensions. Once in place, the tubular member is then expanded to the second configuration with transverse dimensions roughly corresponding to or slightly larger than the body lumen, so that the tubular member can be secured to the wall defining the body lumen. The tubular member may be self expanding or expanded by mechanical devices or by inflation of the balloon of the balloon catheter. The tubular member will then remain in the open configuration implanted in the body lumen.

With the open, lattice-like framework of the tubular member expanded within the body lumen, tissue ingrowth, or epithelialization, through the open framework of the tubular member secures it to the wall defining the body lumen. At the same time, epithelialization through the mesh member occludes the body lumen. Sufficient epithelialization to secure the device to the body wall and occlude the body lumen may take one or more weeks. While the term "epithelialization" is used herein, it should be understood that, depending on the body lumen, tissues such as endothelium or myocardium may be impregnating the device. Additionally, scar tissue formation may take place as well.

One presently preferred embodiment of the invention comprises a reversible contraceptive system which reversibly occludes the reproductive body lumen. The tissue impregnated mesh may be reopened by any number of suitable means. For example, the occluding member may be partially or completely cut away using an atherectomy type catheter or laser to create a lumen, and then compressed using a balloon dilatation catheter similar to an angioplasty procedure. Alternatively, a plug may be releasably secured to the mesh member, so that the plug may be detached from the tissue impregnated mesh member to reopen the lumen. Thus, the contraceptive device of the invention can be left in place to effectively block the passageway until the patient wishes to reverse the procedure.

The contraceptive or sterilization device of the invention provides effective sterilization or contraception for both males and females due to the tissue impregnated mesh member which occludes the reproductive body lumen and which has excellent durability. The device remains in place within the reproductive body lumen, and the tissue impregnated mesh member resists degradation or tearing, to thereby decrease the risk of failure of the device. Moreover, the implantation of the device can be performed in a single office visit, using minimally invasive and easily used devices such as hysteroscopes, catheters, guidewires, guiding catheters and the like. These and other advantages of the invention will become more apparent from the following detailed description of the invention when taken in conjunction with the accompanying exemplary drawings.

DETAILED DESCRIPTION OF THE INVENTION

Figure 1:
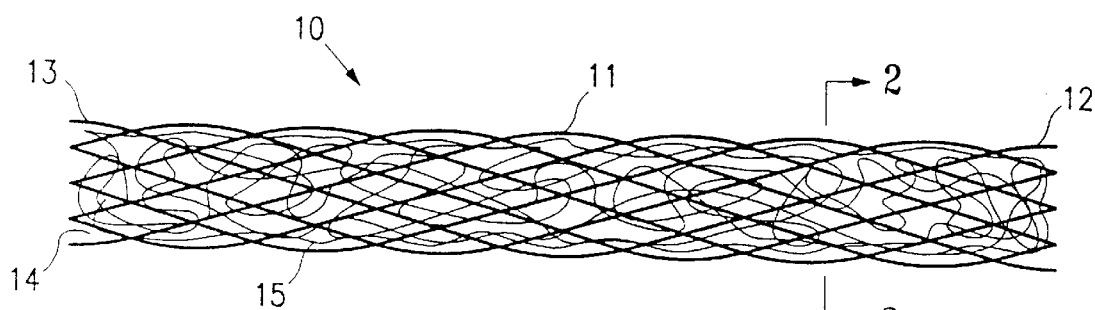
FIG. 1 is an elevational view of one embodiment of the occluding device of the invention with the tubular member in a contracted configuration.
Figure 2:
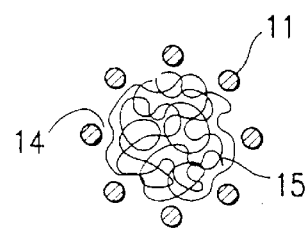
FIG. 2 is a transverse cross sectional view of the device shown in FIG. 1, taken along lines 2—2.

FIG. 1 illustrates an occluding device 10 embodying features of the invention generally comprising a tubular member 11 having a first end 12, a second end 13, and a lumen 14 extending therein. As best shown in FIG. 2, illustrating a transverse cross section of the tubular member shown in FIG. 1 taken along lines 2—2, a mesh member 15 is transversely disposed on the tubular member. In a presently preferred embodiment, occluding device 10 comprises a contraceptive or sterilization device for occluding a reproductive body lumen.

Figure 3:
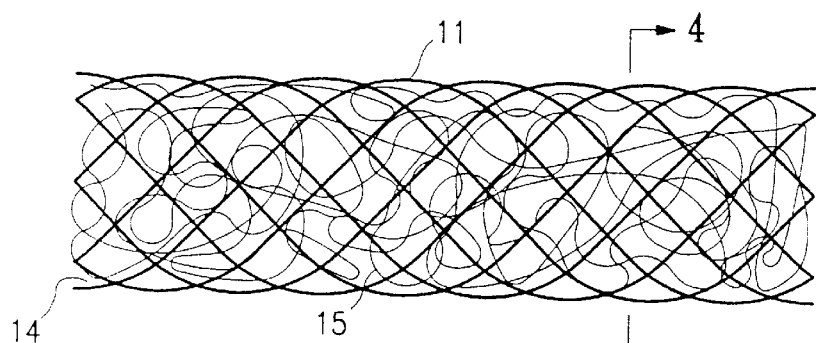
FIG. 3 is an elevational view of the device of the invention shown in FIG. 1, in an expanded configuration.
Figure 4:
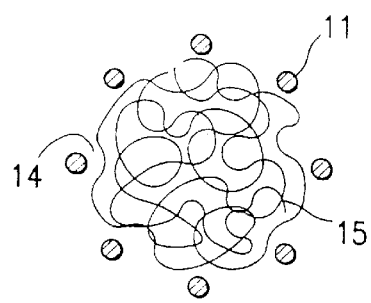
FIG. 4 is a transverse cross sectional view of the device shown in FIG. 3, taken along lines 4—4.

In the embodiment illustrated in FIGS. 1 and 2, the tubular member 11 is in its relatively small dimensioned configuration for introduction and advancement into the patient's body lumen. FIG. 3 illustrates the tubular member 11 shown in FIG. 1 in an open, relatively large dimension configuration. As illustrated in FIG. 4, showing a transverse cross section of the tubular member shown in FIG. 3 taken along lines 4—4, the mesh member 15 expands so that it extends across the expanded lumen 14 of the tubular member 11. In this configuration the tubular member 11 has an open, lattice-type structure facilitating epithelialization which secures the occluding member to the wall defining the body lumen. Preferably, tubular member 11 can be deformed to an expanded diameter, preferably equal to or slightly larger than the dimensions of the body lumen within which the contraceptive device 10 is to be disposed. For disposition within a female patient's fallopian tubes the expanded transverse dimensions should be about 0.1 mm to about 5 mm.

Figure 6:
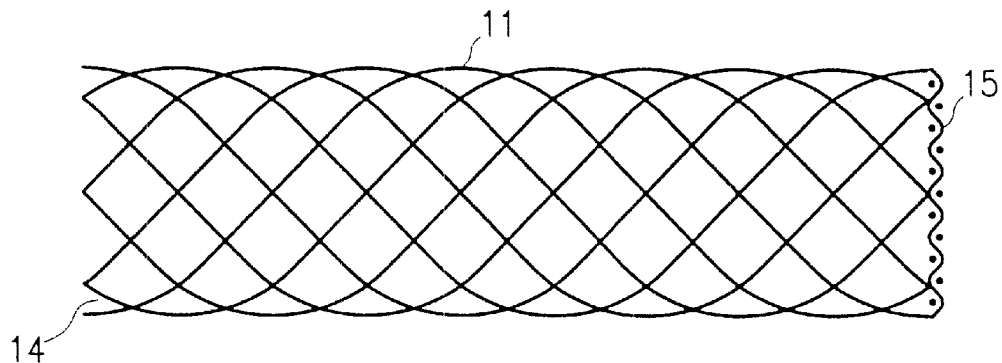
FIG. 6 is an elevational view of another embodiment of the occluding device of the invention having a mesh member comprising woven strands disposed at the first end of the tubular member.
Figure 7:
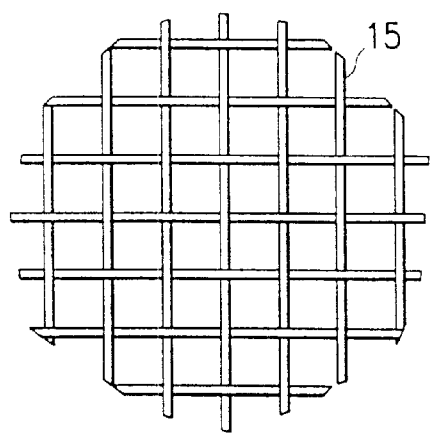
FIG. 7 is a transverse view of the mesh member, shown in FIG. 6, comprising woven strands.

The mesh member 15 is permeable to allow for tissue ingrowth. The permeability of the mesh member 15 facilitates epithelialization, and the epithelialized mesh occludes the reproductive body lumen sufficiently to prevent the passage of reproductive cells therethrough. In a presently preferred embodiment, the mesh member 15 comprises intertwined strands of a biocompatible material connected to the tubular member 11. In the embodiment illustrated in FIG. 1, the mesh member comprises bundled strands. In the embodiment illustrated in FIG. 6 the mesh member comprises woven strands. FIG. 7 is a transverse view of the device illustrated in FIG. 6, illustrating the woven strands forming the mesh member. However, the mesh member 15 may comprise a variety of suitable permeable structures which support epithelialization, as for example, where the mesh member comprises the walls of the tubular member 11 connected together to form a closed end of the tubular member (not shown).

Figure 5:
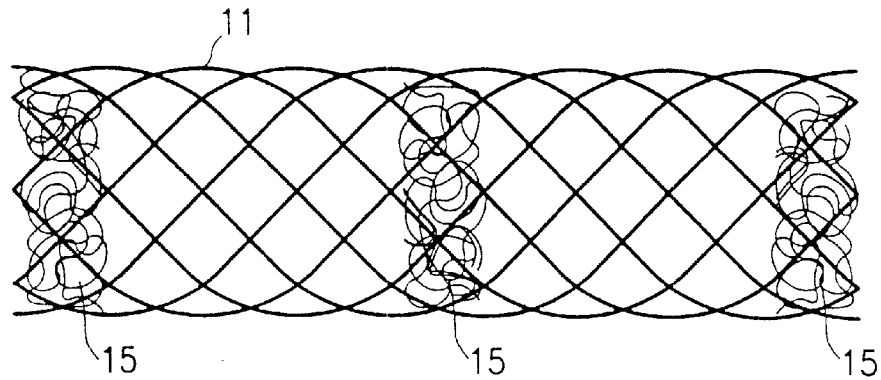
FIG. 5 is an elevational view of another embodiment of the occluding device of the invention having a mesh member comprising bundled strands intermittently spaced in a plurality of sections of the tubular member.

In the embodiment illustrated in FIG. 1, the mesh member 15 extends along the length of the tubular member 11 from the first end 12 to the second end 13 thereof. In another embodiment, illustrated in FIG. 5, the mesh member 15 is disposed in a plurality of sections intermittently spaced along the length of the tubular member. FIG. 6 illustrates another embodiment, in which the mesh member 15 is disposed at the first end of the tubular member 11. In the embodiment illustrated in FIG. 6, the mesh member comprises a single sheet of woven material, disposed in the lumen of the tubular member 11. Alternatively, a plurality of stacked woven mesh sheets may be provided, including sheets having different mesh sizes. In the embodiments illustrated in FIGS. 1, 5 and 6, the mesh member 15 is within the lumen 14 of the tubular member. The mesh member may be connected to the tubular member 11 by a variety of suitable means including adhesive, heat bonding, or solvent bonding.

Figure 8:
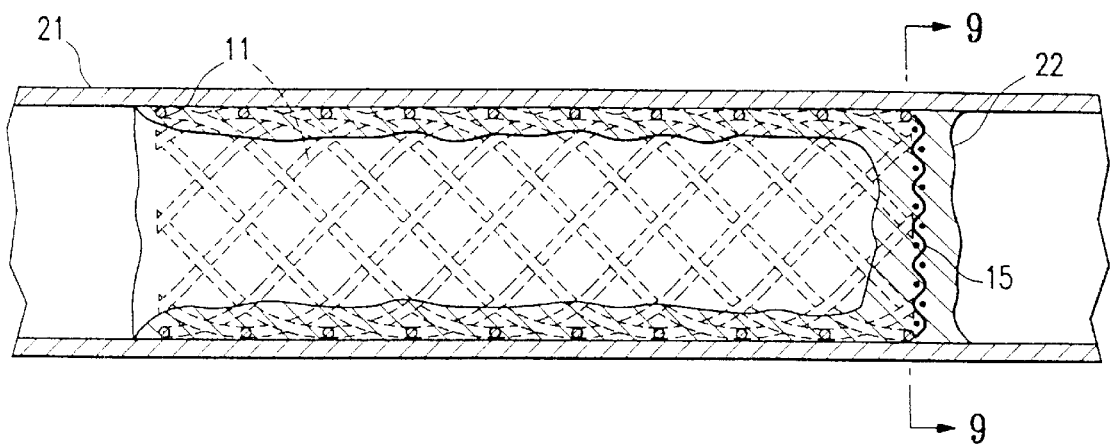
FIG. 8 is a longitudinal cross sectional view of the device shown in FIG. 6, epithelialized in a body lumen.
Figure 9:
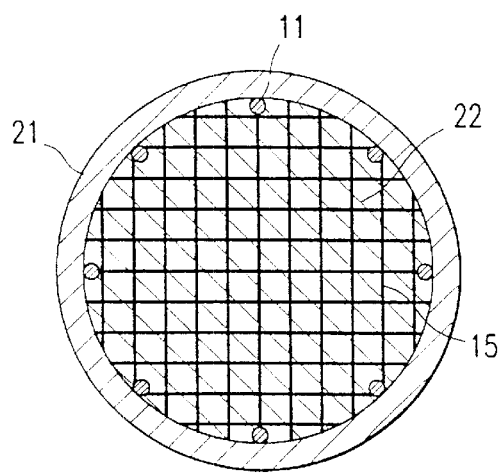
FIG. 9 is a transverse cross sectional view of the device shown in FIG. 8, taken along lines 9—9.

The tubular member 11, expanded within the body lumen to be occluded, epithelializes to secure the contraceptive device 10 within the body lumen, and tissue ingrowth in the mesh member 15 occludes the lumen of the tubular member and the body lumen. FIG. 8 illustrates the embodiment of the contraceptive device 10 shown in FIG. 6, installed within the patient's body lumen 21, with tissue ingrowth 22 within the walls of the tubular member 11 and within the mesh member 15. FIG. 9 illustrates a transverse cross section of the installed device 10 shown in FIG. 8 taken along lines 9—9.

A variety of materials may be used to form the mesh member 15, including plastics, polymers, metals, and treated animal tissues. In a presently preferred embodiment, the mesh member 15 is an irritant, such as Dacron or Nylon, which promotes epithelialization. Additionally, the mesh member may be coated or otherwise impregnated with cell growth stimulators, hormones, and/or chemicals to enhance tissue impregnation. The fibers used to form the mesh member 15 are generally about 0.00025 mm to about 0.25 mm in diameter. It would be obvious that a wide variety of mesh sizes which support epithelialization may be used. For example, in one embodiment the mesh member 15 mesh size is about 5 $\mu$m to about 0.05 mm, and preferably about 10 $\mu$m to about 15 $\mu$m. Preferably, mesh members having relatively large mesh sizes are coated with the epithelialization promoter agents.

Figure 10:
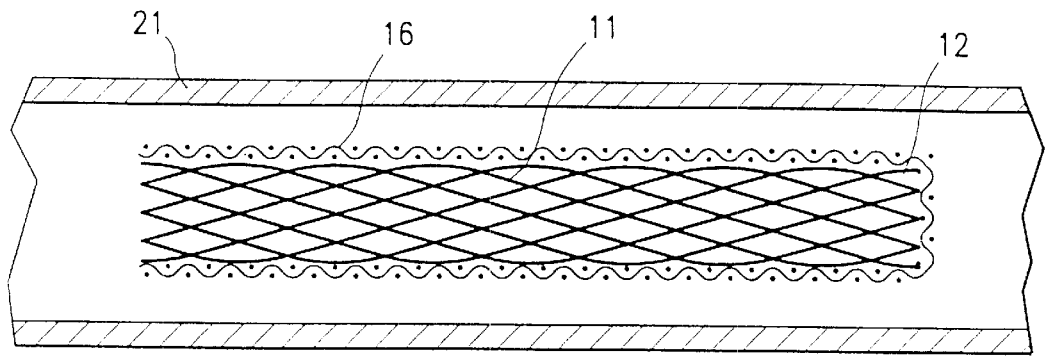
FIG. 10 illustrates another embodiment of the occluding device having a mesh layer on an outer surface of the tubular member, within a body lumen.
Figure 11:
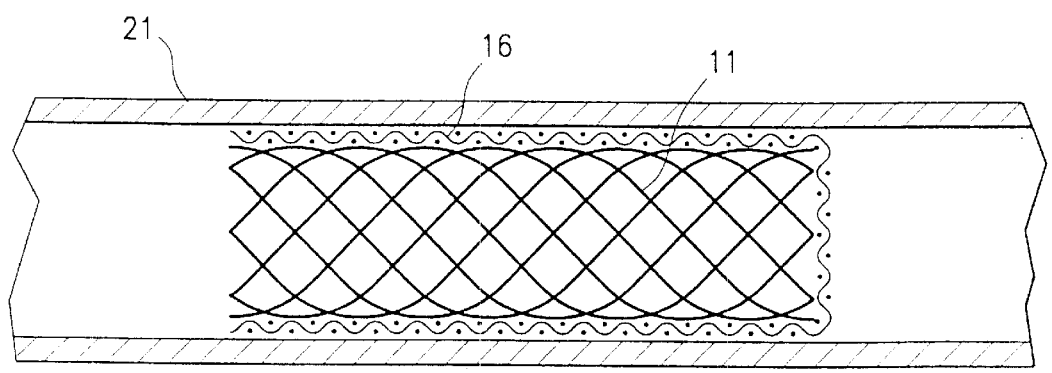
FIG. 11 illustrates the device shown in FIG. 10 in an expanded configuration.

In one embodiment, illustrated in FIG. 10, a mesh layer 16 is provided along at least a section of the outer surface and/or the inner surface of the tubular member, to facilitate tissue epithelialization along the tubular member 11 and into the mesh member 15. In the embodiment illustrated in FIG. 10, the mesh layer 16 is disposed along the entire length of the outer surface of the tubular member 11 and transversely disposed at the first end 12 of the tubular member. The mesh layer may be an integral extension of the mesh member 15, or a separate member connected to or separate from the mesh member 15. In a presently preferred embodiment, the mesh layer 16 comprises woven or bundled strands of a, preferably, biocompatible material, which may be a single or a plurality of mesh sheets, as discussed above in connection with the mesh member 15. The mesh layer is permeable to allow for tissue ingrowth, and consequently, facilitates ingrowth within the mesh member 15, as for example, in embodiments in which only a section of the tubular member is expanded into contact with a wall of the body lumen, as discussed below.

The tubular member 11 may be expanded in the body lumen using a balloon catheter, or alternatively, it may be self expanding. The tubular member is preferably self expanding in the embodiment in which the mesh member 15 is disposed along the length of the tubular member, as in the embodiment illustrated in FIG. 1, or is disposed at least in part at the second end of the tubular member, as in the embodiment illustrated in FIG. 5.

Figure 12:
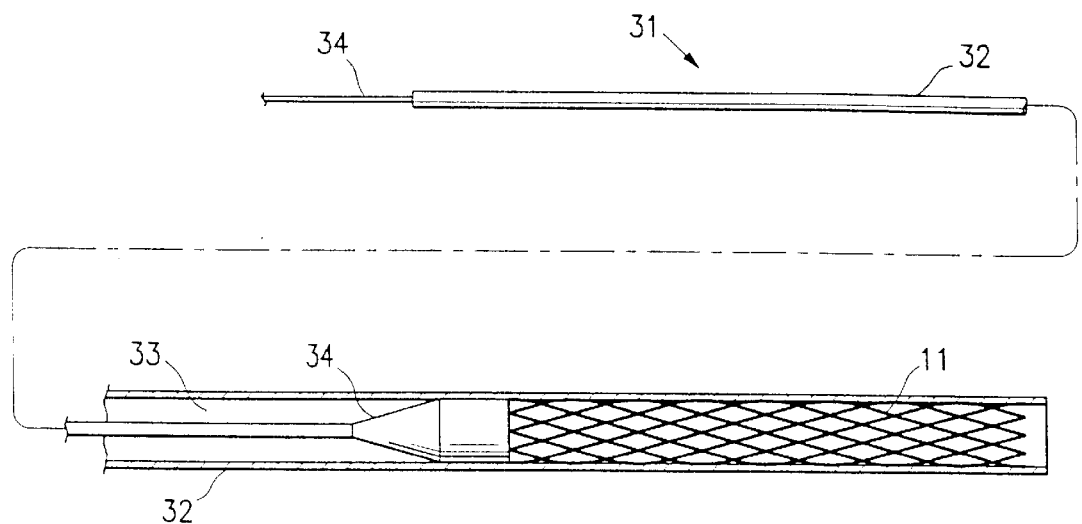
FIG. 12 is an elevational view, partially in section, of a delivery catheter useful in a method of the invention with a self-expanding occluding device of the invention.

FIG. 12 illustrates a delivery catheter 31 useful in the delivery of the device 10 having self expanding tubular member. The delivery catheter 31 generally comprises an elongated shaft 32 having a lumen 33 extending therein. The self expanding tubular member 11 may be deformed into the smaller diameter configuration within the lumen 33 of the delivery catheter, and expanded into the larger diameter configuration within the body lumen by longitudinally displacing the tubular member out the distal end of the delivery catheter to thereby remove the radially compressive force of the delivery catheter. A pusher 34 slidably received within the lumen of the delivery catheter can be used to longitudinally displace the tubular member 11 out the distal end of the delivery catheter.

Figure 13:
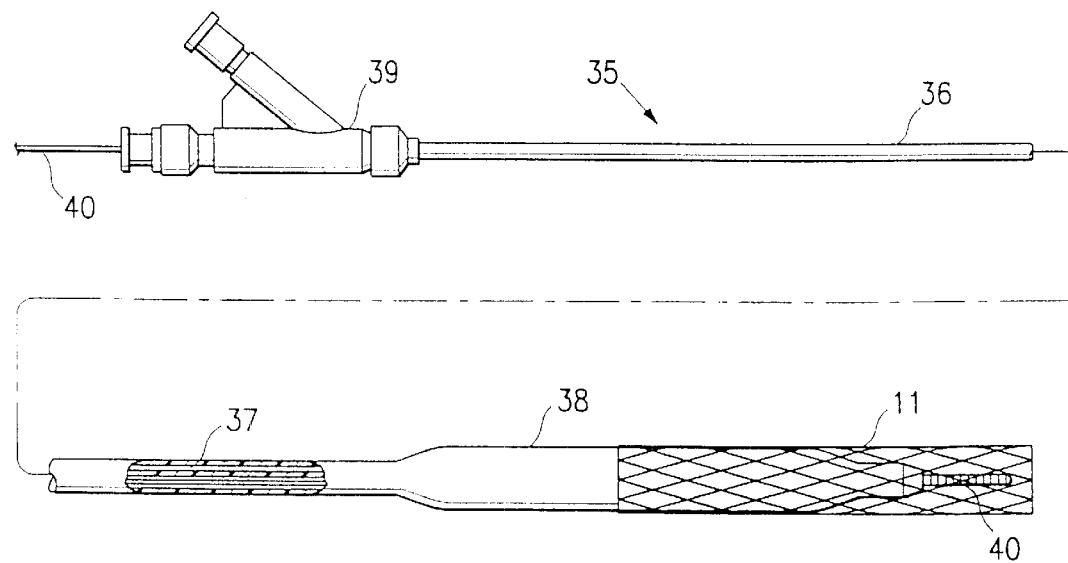
FIG. 13 is an elevational view, partially in section, of a balloon catheter useful in a method of the invention.

Similarly, in the embodiment illustrated in FIG. 6 in which the mesh member 15 is disposed primarily in the first end of the tubular member, the tubular member may be expanded using a balloon catheter inserted into the open second end of the tubular member. FIG. 13 illustrates a catheter 35 useful in the practice of the invention, which comprises an elongated shaft 36 having an inflation lumen 37 which is in fluid communication with inflatable member 38 mounted on a distal section of the catheter shaft, and adapter 39 on a proximal end of the catheter shaft. The tubular member 11 is mounted on the inflatable member 38, and preferably closely conforms to the diameter of the uninflated inflatable member 38 to facilitate introduction into the desired body lumen The tubular member 11 may be deformed to facilitate mounting onto the inflatable member 38, and is expanded by the inflatable member to an open expanded configuration within a body lumen. A guidewire 40 within the catheter lumen may extend through the mesh member 15, provided the guidewire has a relatively small diameter compared with the mesh size. For example, a conventional guidewire having a diameter of about 0.018 inch or less inch may typically be extended through the mesh member 15 without adversely effecting the mesh member 15.

Figure 14:
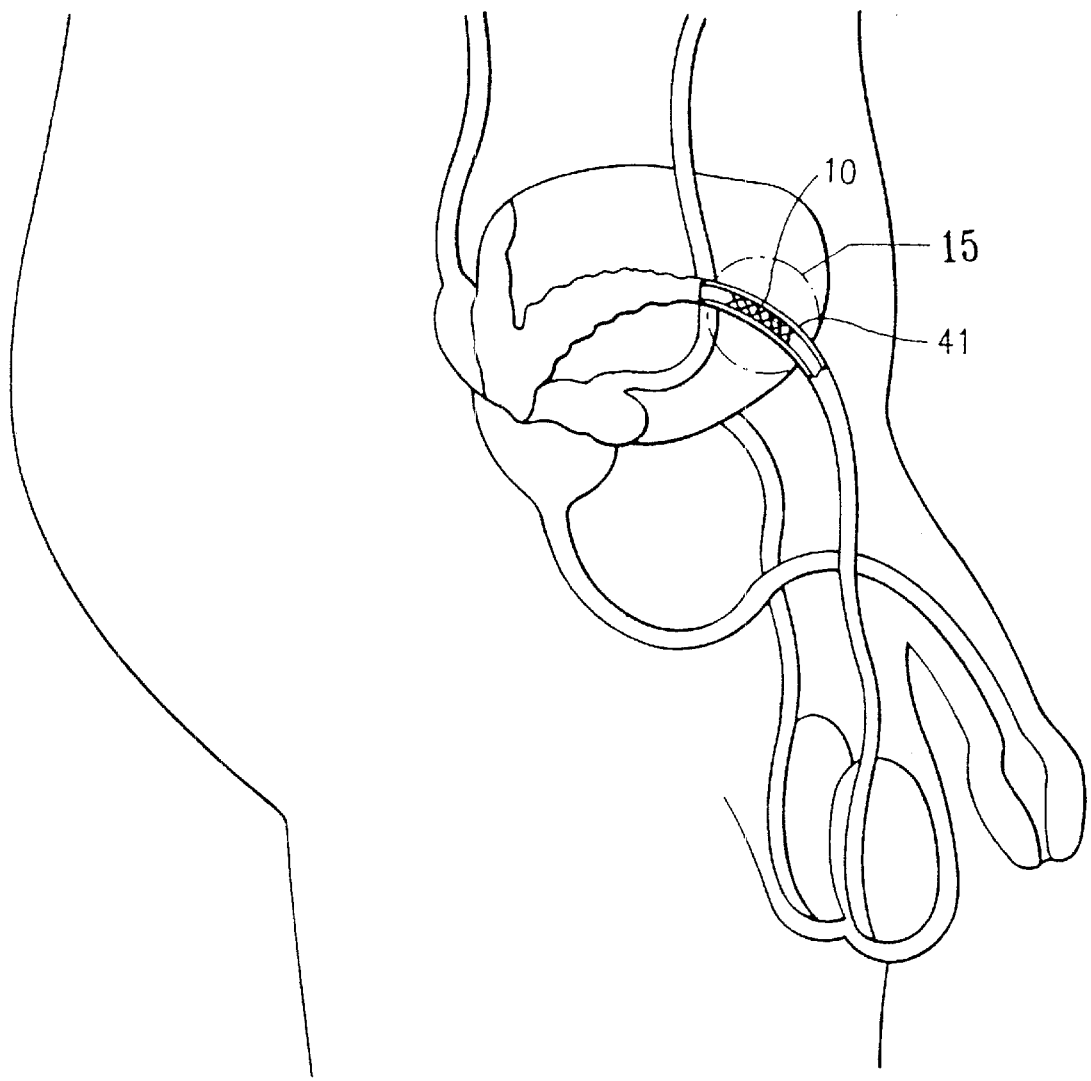
FIG. 14 illustrates the male reproductive anatomy, and a contraceptive device embodying features of the invention, within the vas deferens.
Figure 15:
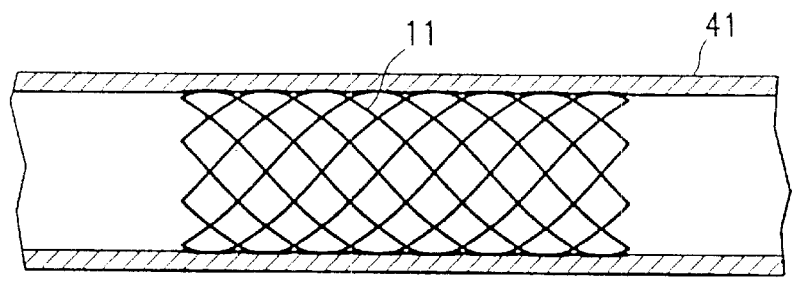
FIG. 15 is an enlarged view of the expanded contraceptive device shown in FIG. 14.
Figure 16:
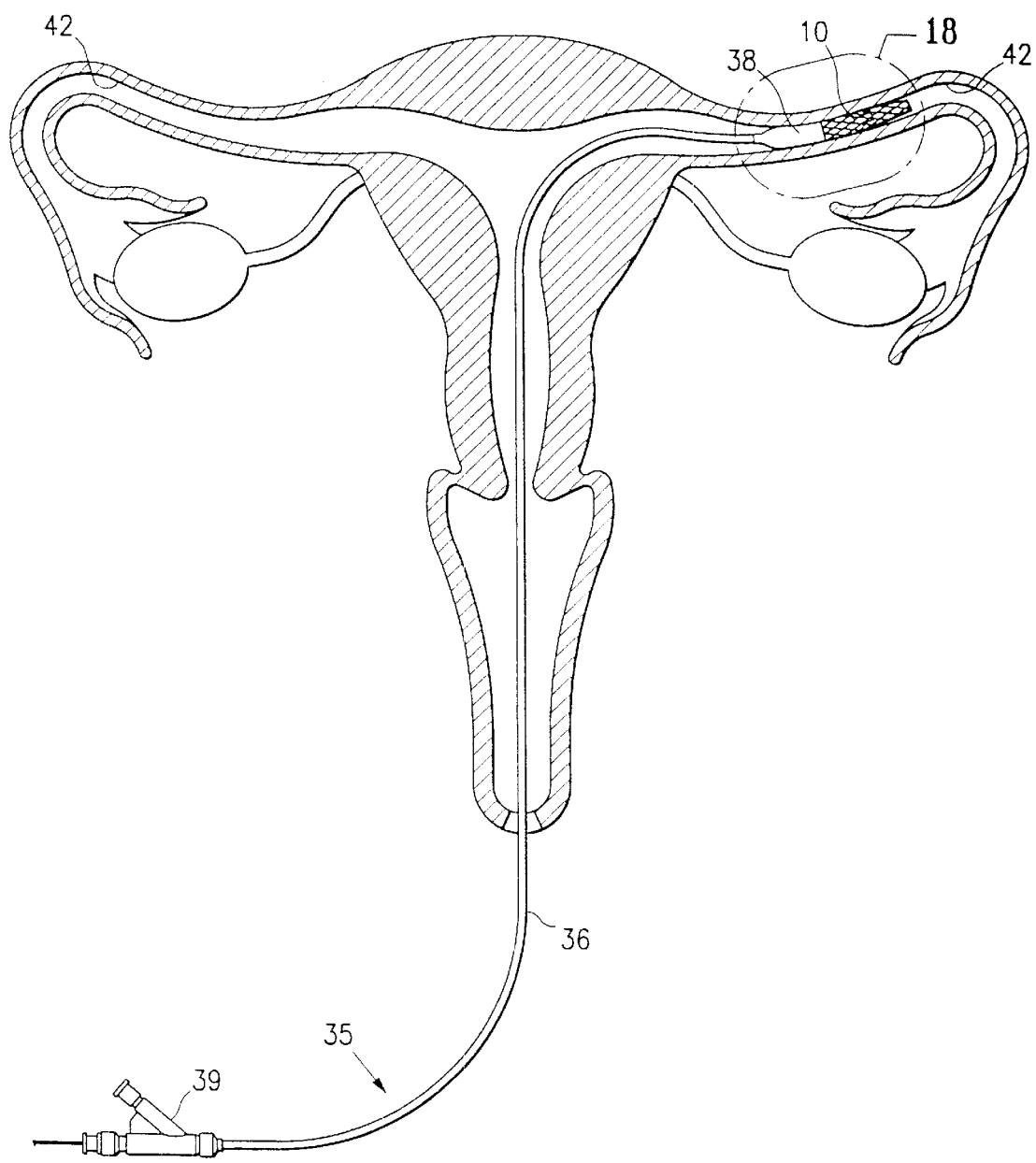
FIG. 16 illustrates the female reproductive anatomy, and a contraceptive device embodying features of the invention, within a fallopian tube.

FIG. 14 illustrates the male reproductive anatomy, including the vas deferens 41 in which the contraceptive device 10 of the invention may be installed. The expanded tubular member 11 within the vas deferens is illustrated in FIG. 15. FIG. 16 illustrates the female reproductive anatomy, including the fallopian tubes 42 in which the contraceptive device 10 is installed. In FIG. 16, the device 10 is shown mounted on the inflatable member 38 of the catheter 35 and positioned within the fallopian tube 42.

Figure 17:
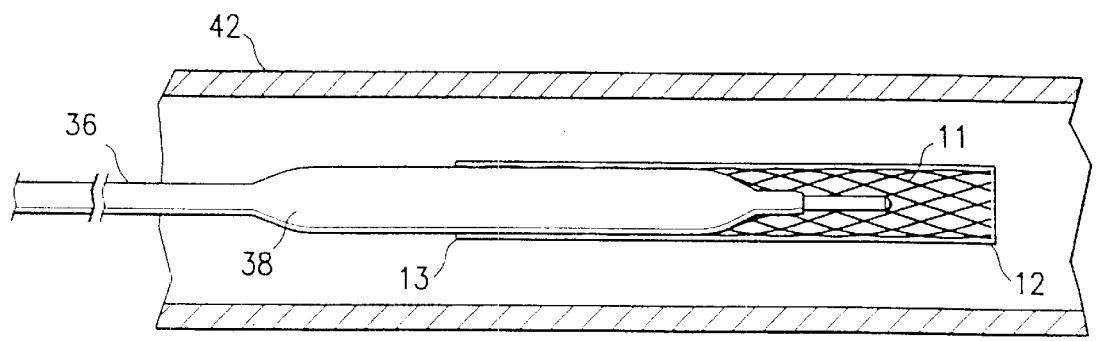
FIG. 17 illustrates the device on a balloon catheter within a reproductive tract or body lumen, with the tubular member in a contracted configuration.
Figure 18:
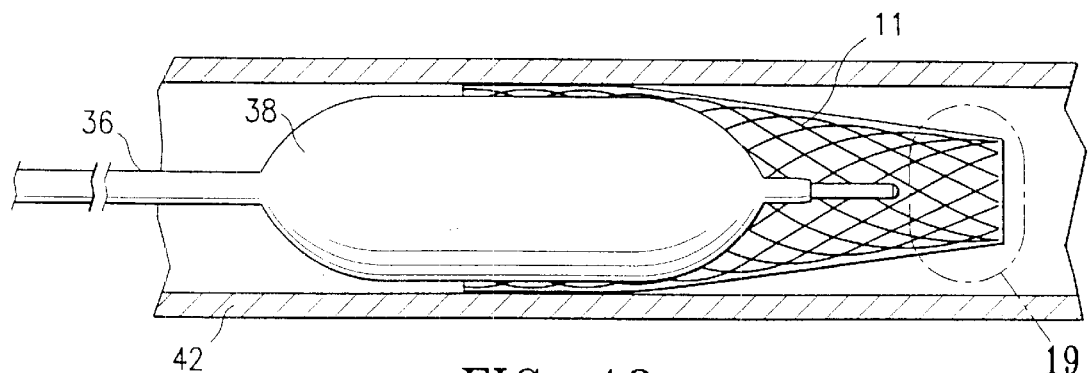
FIG. 18 illustrates the device shown in FIG. 16 within circle 18, with the device on a balloon catheter within the fallopian tube, with the tubular member in an expanded configuration.

The practice of the invention comprises the following general steps, with specific reference to the embodiment illustrated in FIG. 16 comprising a contraceptive device 10 for occluding fallopian tubes of a female patient. The contraceptive device 10 comprising a tubular member 11 having a relatively small transverse dimension is mounted onto the exterior of balloon 38 of catheter 35, as shown in FIG. 17, and the catheter 35 is advanced under fluoroscopic, hysteroscopic, or ultrasonic visualization until tubular member 11 is positioned within one of the female patient's fallopian tubes 42. Inflation fluid is introduced through adapter 39 to inflate inflatable member 38. As shown in FIG. 18, inflation of balloon 38 expands tubular member 11 to an open configuration, lodging it in fallopian tube 42. In the embodiment illustrated in FIG. 18, a section of the tubular member 11 extending from the second end of the tubular member, is expanded into contact with the wall defining the fallopian tube 42. In a presently preferred embodiment, at least about ⅓ of the tubular member is expanded into contact with the body lumen wall to securely attach the device 10 within the fallopian tube 42. The inflatable member 38 is deflated, and the catheter 35 is removed, leaving the expanded tubular member 11 implanted in body lumen 42. Another contraceptive device 10 is delivered to the patient's other fallopian tube and expanded therein in the same manner. Similarly, the tubular member 11 may be expanded into position within the vas deferens 41 of a male patient to provide male contraception using the same procedures. Alternatively, the contraceptive device 10 may be self expanding as discussed above.

Figure 19:
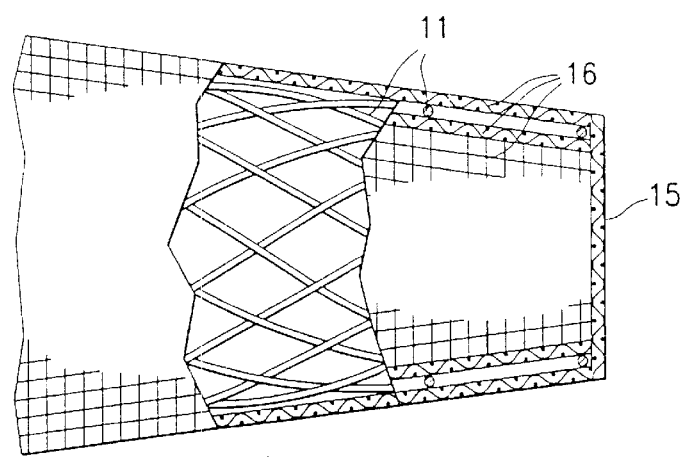
FIG. 19 is an enlarged, partially in section view of the tubular member shown in FIG. 18 within circle 19, illustrating the mesh member and mesh layer.

FIG. 19 illustrates an enlarged, partially in section, view of the first end of the tubular member 11 and mesh member 15 therein, shown in FIG. 18 within circle 19. In the embodiment illustrated in FIG. 19, the mesh layer 16 is on the inner and outer surface of the tubular member 11. Over a period of a week or more epithelial cells lining the lumen will proliferate, growing around the open framework of tubular member 11 and within the mesh member 15, as shown in FIGS. 8 and 9, thereby securing the expanded tubular member 11 to the wall defining the fallopian tube 42, and occluding the fallopian tube 42. In the embodiment illustrated in FIGS. 8 and 9, epithelial cells cover the inner and outer surfaces of the tubular member, so that the tubular member is secured to the fallopian tube as an embedded, integral member therein. The layer of epithelial tissue that forms within the lattice-like structure of the tubular member 11 and optional mesh layer 16 helps block and seal the lumen so as to prevent the passage of reproductive cells, eggs or sperm cells.

Figure 20:
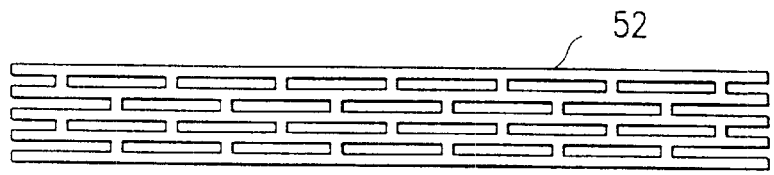
FIGS. 20 and 21 are elevational views of another embodiment of the tubular member comprising a slotted member, in closed and expanded configurations, respectively.
Figure 21:
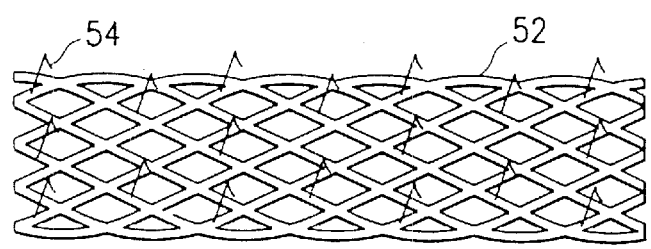
Figure 22:
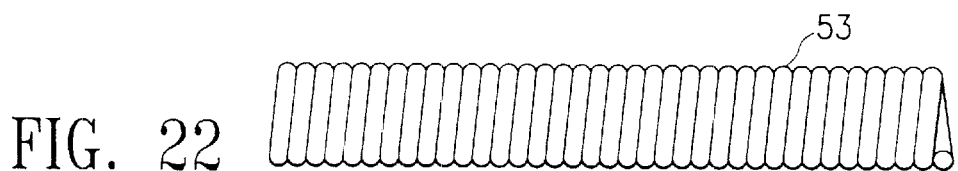
FIGS. 22 and 23 are elevational views of another embodiment of the tubular member comprising a coil, in closed and expanded configurations, respectively.
Figure 23:
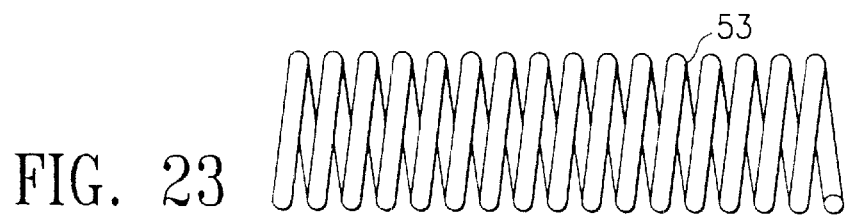

The tubular member may have a number of suitable configurations as shown in schematically in FIGS. 1, 20–23. In the embodiment illustrated in FIG. 1, tubular member 11 comprises a braided tube of wire or ribbon. FIGS. 20 and 21 illustrate another embodiment in which tubular member 11 comprises a length of metal tubing 52, such as hypodermic tubing, having slots. FIG. 20 illustrates tubular member 11 in its relatively small dimensioned configuration for introduction and advancement into the patient's body lumen, and FIG. 21 its larger, open configuration. The slots cut into the wall of the tubing allow expansion of the occluding member into the open configuration shown in FIG. 21. Likewise, in FIGS. 22 and 23, tubular member 11 is a coil 53 of wire or ribbon. It is obvious that a variety of other suitable configurations may be used for tubular member 11, such as a number of closed sinusoidal rings of wire or ribbon.

In still other embodiments, mechanical, adhesive or other anchoring means may be employed to secure the expanded tubular member to the vessel wall defining the body lumen. For example, the means to secure a stent or prosthetic device to an aortic or arterial wall described in U.S. Pat. No. 4,140,126; U.S. Pat. No. 4,562,596; U.S. Pat. No. 4,577,631; U.S. Pat. No. 4,787,899; U.S. Pat. No. 5,104,399; U.S. Pat. No. 5,167,614; U.S. Pat. No. 5,275,622; U.S. Pat. No. 5,456,713; and U.S. Pat. No. 5,489,295 may be used with the present invention to interconnect the wall defining the reproductive tract and the tubular member. These patents are incorporated herein in their entireties by reference. For example, barbs or hooks 54, as illustrated in FIG. 21, may be provided on the tubular member 11. The barbs or hooks become imbedded in the wall defining the body lumen as the tubular member is expanded. Such anchoring members are especially preferred for use in the fallopian tubes of a female patient, in order to prevent the peristaltic action therein from dislodging the device before the epithelialization of the tubular member 11.

The tubular member 11 is formed from metals such as stainless steel, superelastic or shape memory material such as a nickel-titanium (NiTi) alloy such as NITINOL, platinum, tantalum, gold, or rigid or semirigid biocompatible plastics. In a presently preferred embodiment, the tubular member is a superelatic material, providing a controlled force on the body lumen during expansion of the tubular member. The surface of the tubular member's 11 framework may be designed to facilitate epithelial growth, as by providing the tubular member with an open or lattice-like framework to promote epithelial growth into as well as around the member to ensure secure attachment to, and embedment within the wall of the body lumen. Suitable surface techniques include EDM machining, laser drilling, photo etching, sintering and the like. Additionally, increasing the surface area of the tubular member can also provide greater adhesion for the epithelial tissue. Suitable surface treatments include plasma etching, sand blasting, machining and other treatments to roughen the surface. In other embodiments, the device may be coated or seeded to spur epithelialization. For example, the device can be coated with a polymer having impregnated therein a drug, enzyme or protein for inducing or promoting epithelial tissue growth. In yet another refinement, at least part of the device, as for example the tubular member or the mesh layer, could be plated with or otherwise incorporate an inflammatory material to produce an inflammatory response in the tissue of the wall defining the body lumen, which further contributes to the obstruction of the lumen. For example, the mesh member or mesh layer may incorporate strands or particles of inflammatory material therein. In one embodiment the inflammatory material comprises copper or copper alloy. Other inflammatory materials, such as radioactive materials, may be suitable as well. For example, at least a part of the device, as for example the tubular member, could be radioactive, emitting alpha, beta or gamma particles.

Figure 24:
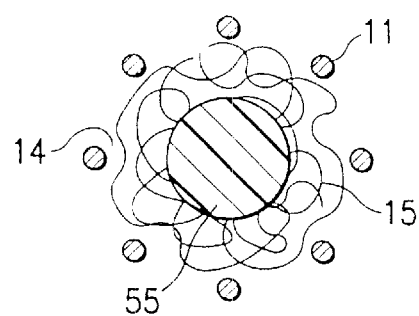
FIG. 24 is a transverse cross sectional view of another embodiment of the invention, having a plug releasably secured to the mesh member.

The occlusion of the lumen may be reversed simply by removing the tissue impregnated mesh, as by cutting away using conventional atherectomy devices or lasers. Additionally, a balloon catheter can be used to compress the occluding tissue ingrowth to open up the passageway. For example, if a passageway larger than the passageway cut into the tissue impregnated mesh is desired, a balloon catheter can be advanced within the body lumen until the balloon is within the lumen left by the cutting of the tissue impregnated mesh and then the balloon on a catheter is inflated to widen the opening. In an alternative embodiment illustrated in FIG. 24, the device 10 further includes a plug 55 releasably secured to the mesh member 15. The plug 55 is secured to the mesh member, as by fusion bonding, biocompatible adhesive, or mechanical connectors, so that the plug may be removed from the implanted device in order to reverse the occlusion of the body lumen by opening up a lumen in the mesh member. A variety of suitable materials may be used to form the plug, including metals and plastics. The plug may be coated or seeded to spur epithelization, or be formed at least in part of an inflammatory material to produce an inflammatory response as discussed above. The plug extends along at least the length of the mesh member, and preferably extends beyond an end of the mesh member.

Various modifications and improvements may be made to the present invention without departing from the scope thereof. For example, while the invention has been discussed primarily in terms of occluding a reproductive body lumen, the device 10 may be used to occlude a variety of body lumens or passageways. A mechanical expandable member such as described in U.S. Pat. No. 4,585,000, which is incorporated herein by reference, may be used to expand the tubular member within the reproductive tract to engage the wall thereof. Moreover, although individual features of embodiments of the invention may be shown in some of the drawings and not in others, those skilled in the art will recognize that individual features of one embodiment of the invention can be combined with any or all the features of one or more of the other embodiments.

What is claimed is:

1. A device for occluding a body lumen or passageway, comprising:
   a) a tubular member having a first end, a second end, a lumen extending therein, and an open-walled structure configured to allow tissue growth therethrough; and
   b) a tissue growth supporting member disposed within at least a section of the tubular member lumen, which is configured to support tissue growth to thereby occlude the body lumen.

2. The device of claim 1 wherein the tissue growth supporting member is permeable to allow for tissue ingrowth.

3. The device of claim 1 wherein the tissue growth supporting member comprises a porous structure.

4. The device of claim 1 wherein the tissue growth supporting member comprises a membranal structure.

5. The device of claim 1 further including a mesh layer longitudinally disposed along at least a section of at least one of an inner and an outer surface of the tubular member.

6. The device of claim 5 wherein the mesh layer is longitudinally disposed along substantially the entire length of the at least one of the inner and the outer surface of the tubular member.

7. The device of claim 1 wherein the tissue growth supporting member is disposed within the lumen of the tubular member along substantially the entire length of the tubular member.

8. The device of claim 1 wherein the tissue growth supporting member is disposed within the lumen of the tubular member in a plurality of sections intermittently spaced along the length of the tubular member.

9. The device of claim 1 wherein the tissue growth supporting member is disposed within the lumen of the tubular member at the first end of the tubular member.

10. The device of claim 9 including a mesh layer longitudinally disposed along at least a section of at least one of an inner and outer surface of the tubular member.

11. The device of claim 1 wherein the tubular member comprises a material selected from the group consisting of stainless steel, superelastic material, shape memory material, rigid plastics, semirigid plastics, metal, NiTi, tantalum, platinum, and gold.

12. The device of claim 1 wherein the tubular member further includes anchoring members configured to secure the tubular member to a wall defining the body lumen.

13. The device of claim 1 wherein the tubular member expands from a first configuration to a second larger configuration by the release of a radially compressive force.

14. The device of claim 13 wherein the tubular member comprises a superelastic material.

15. The device of claim 9 wherein the tubular member expands from a first configuration to a second larger configuration, and the second larger configuration comprises a radially expanded diameter increasing along at least a section thereof from the first end of the tubular member to the second end of the tubular member.

16. The device of claim 1 wherein the tubular member comprises a lattice-like framework.

17. The device of claim 16 wherein the lattice-like framework comprises a thin walled metallic tube having a pattern of cuts configured to allow the tubular member to be expanded to a large diameter configuration.

18. The device of claim 16 wherein the lattice-like framework comprises a braid of wire.

19. The device of claim 16 wherein the lattice-like framework comprises a helical coil of wire.

20. The device of claim 1 wherein the surface of the tubular member is configured to promote epithelialization.

21. The device of claim 1 coated at least in part with a compound to promote tissue cell growth.

22. The device of claim 1 further comprising a material capable of provoking an inflammatory response.

23. The device of claim 22 wherein the inflammatory material comprises copper or copper alloy.

24. The device of claim 22 wherein the inflammatory material comprises a radioactive material.

25. The device of claim 1 wherein the tubular member has an expanded portion and said open-wall structure facilitates the ingrowth of tissue cells thereby securing at least a section of the expanded portion of the tubular member to a wall portion of the body lumen.

26. The device of claim 1 further including a plug releasably secured to the tissue growth supporting member.

27. The device of claim 26 wherein the plug is formed at least in part of a material capable of provoking an inflammatory response.

28. The device of claim 1 wherein the tissue growth supporting member extends transversely across the lumen of the tubular member.

29. A device for occluding a body lumen or passageway, comprising:
   a) an open-walled coil member having a first end, and a second end and a lumen extending therein; and
   b) a tissue growth supporting member disposed within at least a section of the coil member lumen, which is configured to support tissue growth to thereby occlude the body lumen or passageway.

30. A contraceptive device installed within a lumen of the patient's reproductive system, comprising
   a) an open-walled coil member having a first end, a second end, and a lumen extending therein, and having at least a portion thereof which is secured to a body wall portion defining at least in part the lumen of the patient's reproductive system; and
   b) an occluding member disposed within at least a section of the lumen of the coil member, comprising an epithelialized tissue growth supporting member which occludes the lumen of the patient's reproductive system sufficiently to prevent the passage of reproductive cells therethrough.

31. The installed contraceptive device of the claim 30 wherein the coil member is epithelialized along at least a length thereof.

32. A contraceptive system, comprising
   a) a catheter having a proximal end, a distal end, and a lumen extending at least in part therein; and
   b) a contraceptive device releasably connected to the catheter, having a tubular member having a first end, a second end, a lumen extending therein, and an open-walled structure, and having a tissue growth supporting member disposed within at least a section of the lumen of the tubular member, which is configured to support tissue growth to thereby occlude the reproductive body lumen.

33. The contraceptive system of claim 32 including an expanding member on a distal section of the catheter to expand at least a portion of the tubular member.

34. A method of contraception comprising the steps of:
   a) inserting within a desired body lumen a contraceptive device comprising an open-walled tubular member and a tissue growth supporting member disposed within at least a section of the tubular member;
   b) expanding the tubular member within the body lumen;
   c) securing the expanded tubular member to a wall portion defining at least in part the body lumen; and
   d) epithelializing the tissue growth supporting member to occlude the body lumen.

35. The method of claim 34 wherein the step of securing the tubular member to the wall portion comprises epithelializing the tubular member within the body lumen.

36. The method of claim 35 wherein the contraceptive device further includes one or more connecting members on a surface of the tubular member, and wherein the step of securing the tubular member to the wall portion further comprises embedding the connecting members in the wall portion.

37. The method of claim 34 wherein the contraceptive device is disposed on an expandable member of a delivery catheter, and wherein the step of expanding the tubular member comprises inflating the expandable member.

38. The method of claim 37 wherein the tissue growth supporting member of the contraceptive device is transversely disposed within a lumen of the tubular member at a first end of the tubular member, and a distal end of the expandable member of the catheter is disposed in the tubular member lumen proximal to the tissue growth supporting member, and the step of inflating the expandable member expands the tubular member to a larger diameter increasing along at least a section of the tubular member from a second end to the first end of the tubular member.

39. The method of claim 38 wherein at least the second end of the tubular member is expanded into contact with the wall portion of the body lumen.

40. The method of claim 39 further including the step of deflating the expandable member and withdrawing the delivery catheter from the body lumen.

41. The method of claim 34 wherein the step of expanding the tubular member comprises the step of releasing a radially compressive force on the tubular member.

42. The method of claim 41 wherein the contraceptive device is disposed within a lumen of a delivery catheter, and the step of releasing the radially compressive force comprises longitudinally displacing the tubular member out a distal end of the delivery catheter.

43. The method of claim 34 wherein the expanded tubular member is disposed within the body lumen for sufficient time for it to be epithelialized within the body lumen and thereby secured to the wall portion.

44. A device for occluding a body lumen or passageway, comprising:
   a) a tubular member having a first end, and a second end, and a lumen extending therein, which is at least in part expandable within the reproductive body lumen from a first configuration to a second larger configuration; and
   b) a tissue growth supporting member disposed within at least a section of the tubular member lumen, which is configured to support tissue growth to thereby occlude the body lumen or passageway.

45. The device of claim 44 wherein the tissue growth supporting member comprises bundled fibers.

* * * * *

UNITED STATES PATENT AND TRADEMARK OFFICE
CERTIFICATE OF CORRECTION

PATENT NO. : 6,432,116 B1
DATED : August 13, 2002
INVENTOR(S) : Jeffrey P. Callister et al.

It is certified that error appears in the above-identified patent and that said Letters Patent is hereby corrected as shown below:

Title page,
Item [63], Related U.S. Application Data, delete "Continuation" and insert
-- Continuation-in-part of application Serial No. 08/770,123, filed December 18, 1996 and a continuation --

Column 1,
Line 7, after "6,096,052," delete "both of" and after "which" change "are" to -- is --.

Column 12,
Line 34, insert -- 46. The device for occluding a body lumen, comprising:
 a) tubular member having a first end, a second end, and a lumen extending therein, which is at least in part expandable in the body lumen from a first inner and outer diameter to a second greater inner and outer diameter configured to secure the tubular member to a wall defining the body lumen; and
 b) a tissue growth supporting member disposed within at least a section of the tubular member lumen, extending transversely across the lumen of the tubular member and configured to support tissue growth to thereby occlude the body lumen. --

Signed and Sealed this

Eleventh Day of May, 2004

JON W. DUDAS
*Acting Director of the United States Patent and Trademark Office*